(12) United States Patent
Möller et al.

(10) Patent No.: US 7,629,486 B2
(45) Date of Patent: Dec. 8, 2009

(54) METHOD FOR PRODUCING AMINO- OR HYDROXYBENZONITRILES

(75) Inventors: Roland Möller, Hammersbach (DE); Mario Gómez, Pfungstadt (DE); Klaus Einmayr, Tacherting (DE); Jens Hildebrand, Hildesheim (DE); Hans-Georg Erben, Stephanskirchen (DE); Hans-Peter Krimmer, Kirchweidach (DE)

(73) Assignee: AlzChem Trostberg GmbH, Trostberg (DE)

( * ) Notice: Subject to any disclaimer, the term of this patent is extended or adjusted under 35 U.S.C. 154(b) by 173 days.

(21) Appl. No.: 11/791,579

(22) PCT Filed: Nov. 29, 2005

(86) PCT No.: PCT/EP2005/012749

§ 371 (c)(1),
(2), (4) Date: Jun. 8, 2007

(87) PCT Pub. No.: WO2006/058710

PCT Pub. Date: Jun. 8, 2006

(65) Prior Publication Data

US 2007/0265462 A1    Nov. 15, 2007

(30) Foreign Application Priority Data

Dec. 1, 2004 (DE) .................. 10 2004 058 001
Nov. 15, 2005 (DE) .................. 10 2005 054 362

(51) Int. Cl.
*C07C 253/00* (2006.01)
(52) U.S. Cl. .................................... 558/311
(58) Field of Classification Search .............. 558/311
See application file for complete search history.

(56) References Cited

FOREIGN PATENT DOCUMENTS

| DE | 195 20 491 A | | 12/1996 |
|----|--------------|---|---------|
| DE | EP 745585 | * | 12/1996 |
| GB | 1 220 386 B A | | 1/1971 |
| JP | 63 243064 A | | 10/1988 |
| WO | WO-03/097582 A | | 11/2003 |

OTHER PUBLICATIONS

Erben, 1997, CAS: 126:74606.*

* cited by examiner

*Primary Examiner*—Rei-tsang Shiao
(74) *Attorney, Agent, or Firm*—Fulbright & Jaworski L.L.P.

(57) ABSTRACT

The invention relates to a method for producing amino- or hydroxybenzonitriles during which, within the scope of an ammonolysis, the corresponding amino- or hydroxybenzoic acid compounds are reacted with ammonia in the presence of a phosphate-containing supported catalyst at temperatures between 250° C. and 500° C. The production step is carried out in a reaction gas without an organic solvent followed by at least a 2-stage purification step.

23 Claims, No Drawings

METHOD FOR PRODUCING AMINO- OR HYDROXYBENZONITRILES

This is a §371 of PCT/EP2005/012749 filed Nov. 29, 2005, which claims priority from German Patent Application Nos. 10 2004 058 001.4 filed Dec. 1, 2004 and 10 2005 054 362.6 filed Nov. 15, 2005.

The present invention provides a novel process for preparing amino- or hydroxybenzonitriles, in which a preparation step 1) is combined with a purification step 2).

Amino- and hydroxybenzonitriles are products in which there is increasingly great interest, and hydroxybenzonitriles in particular find use as intermediates in the preparation of plant-active ingredients.

In the preparation of aromatic nitrites, there are numerous different variants, of which ammoxidation of methylarenes has to date been at the forefront with regard to the amino- or hydroxybenzonitriles. Examples here include the German published specification DE 20 20 866 and the French patent FR 2 332 261.

Typically, hydroxybenzonitriles are prepared via the amination of an alkyl hydroxybenzoate which is followed by a dehydration reaction. The German published specification DE 20 20 866 A1 discloses a process for preparing 4-hydroxybenzonitrile, the reaction of ammonia and methyl 4-hydroxybenzoate being performed in the gas phase and in the presence of a supported phosphoric acid catalyst, i.e. as a typical ammonolysis.

A similar reaction is described in the patent FR 2 332 261, in which, however, in contrast to the process just mentioned, a catalyst which consists of borophosphate doped with a transition metal is used. A significant problem in this reaction type is that the product obtained therefrom, specifically the hydroxybenzonitrile compounds, solidify in the course of condensation, which complicates the product removal. Moreover, by-products which arise, for example, from a trimerization of the resulting products to s-triazine, which proceeds especially at high temperatures, are formed in this reaction mode. A further side reaction proceeds as the hydrolysis of the resulting 2-hydroxybenzonitrile to 2-hydroxybenzamide, which is accelerated especially by amounts of water which are released in the course of the preparation of the nitrile. This hydrolysis is enhanced by the presence of ammonia.

Compared to the often-used fixed bed processes, fluidized bed reactions have the advantage that the catalysts used are much more stable, since they have a lesser tendency to cake and form channels. These disadvantages with regard to the catalysts can also be discerned from the cited German published specification and the French patent, since they employ catalysts which have precisely the negative properties described.

For this reason, for example, in the German published specification DE 195 20 491 A1, a process has been proposed for preparing amino- or hydroxybenzonitriles which employs catalysts which have high attrition resistance and can therefore be used especially in a fluidized bed process. The catalysts described there have a high loading, which makes possible a high space-time yield and a highly economically viable preparation of the nitrites mentioned. In addition, the catalysts described in this German published specification feature a high selectivity.

The catalysts according to DE 195 20 491 A1 are supported borophosphate catalysts which have been doped with transition metal compounds of group 5, 6, 12 or 14 of the Periodic Table of the Elements or combinations thereof and whose specific surface area is at least 400 m²/g.

Although it is possible with the aid of these supported catalysts to achieve yields and selectivities up to 100% and the catalysts withstood a loading of up to 5 mol of starting material per kg of catalyst and hour, the removal of the desired products still presents problems.

There are thus increasing efforts to undertake process improvements which simplify the removal in particular of hydroxybenzonitriles.

At this point, reference is made in particular to international application WO 01/96 284, which describes a process for removing a compound of the hydroxybenzonitrile type, the end products being obtained with the aid of an amidation/dehydration process. 2-Hydroxybenzonitrile (2-cyanophenol) in particular is at the forefront of the considerations presented there.

The removal described in this application proceeds from a crude product which is obtained from a gaseous reaction stream in the form of an ammonium salt. Thus, the main purification step also consists in displacing ammonium ions, which is effected in particular with a physical treatment of the gaseous reaction stream. However, it is also possible to physically treat the solid obtained beforehand from the gaseous reaction stream by liquefaction or to treat the solid brought into solution. A chemical treatment on the liquefied gaseous reaction stream is likewise proposed.

What is notable in all processes for preparing amino- or hydroxybenzonitriles practiced commercially to date is the fact that they proceed from esters or else, in the case of acids, first convert these acids to acid amides, before the reaction to the nitrites proceeds. Since acids as starting materials, especially in the gas phase, tend to decompose at the usually high temperatures, there has been a transition to using their esters, which, though, in turn has an adverse effect on the product purity owing to alcohols formed and accompanying aromatic by-products.

The prior art and the associated disadvantages has suggested the object of the present invention, that of providing a process for preparing amino- and hydroxybenzonitriles of the general formula (I)

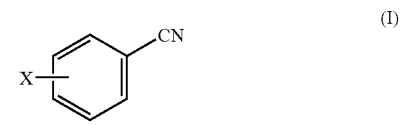

(I)

in which X is at least one amino or hydroxy group, by reacting an amino- or hydroxybenzoic acid compound of the general formula (II)

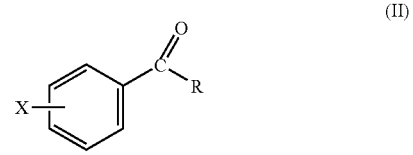

(II)

where R=—OH or —NH$_2$, and X is as defined above, with ammonia in the presence of a supported catalyst comprising phosphorus at temperatures between 250 and 500° C. The selection of suitable process steps with regard to the preparation should afford a crude product whose form ensures the subsequent purification in economically viable form, and the isolated end product should have a high purity. In particular, by-products which are otherwise customary should be suppressed or completely eliminated, and both the preparation process and the purification process should satisfy requirements from an environmental point of view which additionally make it attractive from an economic point of view.

This object is achieved by a process in which preparation step 1) is performed in a reaction gas (mixture) and without involvement of an organic solvent and is then followed by an at least two-stage purification step 2) in which 2.1) the gaseous mixture obtained from preparation step 1) is converted to an aqueous basic suspension and 2.2) the product present in the solid is then released from this suspension.

The objective has been fulfilled in particular in that the process according to the invention is performable in a much more economically viable and inexpensive manner than, for example, similar processes in which the acid amide obtained initially from the corresponding amino acid or hydroxy acid is reacted with phosgene to give the nitrile. The salt concentrations which are obtained in relatively large amounts from this process are entirely avoided or greatly reduced, and the acids used which have not been converted can be recycled. An additional factor is that the process according to the invention can afford an extremely pure product which has dramatically reduced phenol and alcohol contents as otherwise typical by-products.

Surprisingly, it has additionally been found, for the fulfillment of the objective, that the process according to the invention has for the first time overcome the preconception known to date from the prior art, specifically that aromatic nitriles can be prepared in an economically viable manner exclusively from their corresponding acid esters. This is because, as has been shown, not only the esters which have been used to date owing to their thermal stability and better handling can be used. As the present invention shows, it is also possible to use the aromatic acids in aminated and hydroxylated form as likewise very suitable starting compounds. In addition to their economic advantage, which can be discerned in significantly lower cost, another extremely advantageous fact which has been found is that the alcohols which are typically otherwise present in the esters now no longer contaminate the intermediates and end products and also no longer have to be disposed of. In particular, further by-products, as are formed, for example, by an undesired chlorination or alkylation owing to alcohol traces present, can be avoided.

These advantages of the novel process, but in particular the overcoming of the preconception that acids, under ammonolytic conditions, cannot be used as direct starting compounds for the preparation of amino- or hydroxybenzonitriles, were thus unexpected.

As can be taken from the statements regarding preparation step 1), the process according to the invention in this regard is a typical ammonolysis. This as preparation step 1), but also the purification step 2), are not fixed to particular temperature ranges, but it has been found to be favorable to perform preparation step 1) at temperatures between 340 and 450° C. and more preferably between 380 and 420° C.

An essential factor for the success of the combination process claimed is that of the use of suitable catalysts. In this regard, reference is made in particular to German published specification 195 20 491, in which the doped supported borophosphate catalysts also used with preference in the present process according to the invention are described in detail.

Thus, for the present process, generally a supported catalyst comprising phosphorus which has been doped with transition metal compounds of groups 5, 6, 12 and 14 of the Periodic Table of the Elements or combinations thereof and which has a specific surface area of at least 300 $m^2/g$ is used. Preference may also be given to using a supported catalyst which has additionally been doped with boron. In this case, the proportion of borophosphate should be between 0.01 and 15% by weight, and proportions between 0.5 and 5% by weight, based in each case on the weight of the support material, are considered to be particularly suitable.

With regard to the preparation of such a supported borophosphate catalyst, the present invention is subject to no restriction. However, particularly suitable supported catalysts have been found to be those which have been prepared by treating the support material with aqueous solutions of from 0.01 to 15% by weight of phosphoric acid, from 0.01 to 15% by weight of boric acid and from 0.01 to 5% by weight of salts of transition metals of group 5, 6, 12 or 14 of the Periodic Table of the Elements or combinations of such salts. These salts of the transition metals are partially dissolved in the initially charged solution and subsequently stirred at room temperature for approx. 1 hour. For this purpose, preference is given to using salts which consist of cations of the particular elements and of the borate, chloride, phosphate or sulfate anion. However, it is possible to form the salts from the anions of the particular elements and ammonium as the cation.

Preferred cations for the supported catalyst are those of vanadium, niobium, tantalum, chromium, molybdenum, tungsten, cadmium, mercury, germanium, tin, lead or zinc, and it is of course also possible again to use combinations of corresponding salts.

Typically from 20 to 80% by weight of a support material selected from the group of silicon dioxide, silica gel, aluminum oxide, titanium oxide or zirconium oxide or mixtures thereof is added to the initially charged solutions comprising the corresponding cations and anions. This support material should have a specific surface area of at least 400 $m^2/g$. The water is subsequently evaporated, which can also be effected using vacuum, and the resulting crude catalyst is dried at temperatures between 100° C. and 500° C. for a maximum of 3 hours, and it has been found to be favorable to pass a gentle air stream over it. A particularly suitable drying temperature has been found to be the range between 140° C. and 160° C. The supported catalyst thus preparable, in accordance with the invention, has a specific surface area which is more than 400 $m^2/g$. Particularly advantageous specific surface areas are considered to be those which are >500 $m^2/g$, >600 $m^2/g$ and in particular 750 $m^2/g$. The pore diameter of the supported catalyst should preferably be between 0.4 nm and 25 nm and in particular between 0.5 nm and 15 nm.

With regard to the actual preparation step 1) for the amino- or hydroxybenzonitriles, in the context of the present invention, a reaction gas (mixture) which is oxygen-free and/or predominantly ammonia-containing is used. This reaction gas (mixture) is of particular significance for the process according to the invention, since it can be used as inert gas and/or can also function as carrier gas.

For the preparation step 1), which is performed exclusively in the gas phase, it may additionally be advantageous when the amino- or hydroxybenzoic acid compound is introduced into the reaction gas (mixture) and/or the catalyst bed, which can also be effected by spraying into or onto the catalyst and which is likewise included in the present invention. The particular starting compounds can preferably be applied to the catalyst as an acid or acid amide (aqueous solution of an ammonium salt), as a melt or in the form of a solid.

As already mentioned explicitly, preparation step 1) of the combination process according to the invention succeeds without the acid compounds used decomposing in the gas phase, which is possibly attributable to a stabilizing effect of the ammonia gas used, which suppresses or completely prevents the decarboxylation tendencies otherwise observed when acid is used. It should be emphasized that the product in the process according to the present invention is present in the gas phase only when it leaves the reactor, which is why lasting effects, for example trimerization reactions, are avoided. It should also be emphasized that the product obtainable from preparation step 1) is normally obtained in the form of a white to light brown and fluffy, flaky product which is easy to obtain and should be fed to the subsequent two-stage purification step 2).

Suitable temperatures advantageous for the purification step 2) of the process according to the invention have been found to be a range between −20° C. and 100° C., and the ranges between 0° C. and 60° C. and especially between 2° C. and 7° C. have been found to be particularly recommended for particular process variants.

As already emphasized, the reaction gas (mixture) used in preparation step 1) should be essentially oxygen-free, but it may be necessary to perform the purification step 2) additionally under inert gas conditions and, in this case, preferably in a nitrogen atmosphere to avoid any disruptions.

With regard to the purification step 2), it should be emphasized as essential to the invention that the gaseous mixture obtained first from preparation step 1) is converted to an aqueous basic suspension. For this purpose, the present invention recommends the use of a quench which is preferably performed with water or ammoniacal water. The ammoniacal water, which of course has a basic character, should be used in particular if a product present in solid form is to be quenched.

In order to actually obtain a suspension for purification step 2.2, it is advisable first to cool the products obtained from preparation step 1) and then to take up the resulting solid with ammoniacal water.

Irrespective of whether the aqueous basic suspension is obtained with the aid of a quench or by cooling and a subsequent absorption, it may be necessary for the product quality in the context of the process claimed to initially charge an aqueous basic suspension in highly concentrated form, in which the by-products are present in dissolved form.

This is because it is possible to remove the end product and the by-products particularly effectively and with a low degree of complexity from these suspensions, since the particular product groups are already present in different states of matter.

The last part-step of purification step 2) consists in releasing the product present in the solid from the aqueous basic suspension obtained from process step 2.1). For this release, the process according to the invention envisages acidic conditions, as a result of which the product which is preferably present as an ammonium salt in the solid is obtained in pure form.

With regard to this release, three variants are possible in accordance with the invention, which can also be combined with one another if required:

Variant 1 consists in effecting the release with the aid of a filtration and with addition of acid or else alternatively by driving out ammonia and the subsequent introduction of the acid component. To ensure the acidic conditions, the addition of an acid is advisable, for which mineral acids and especially hydrochloric acid have been found to be particularly suitable. However, it is also possible to introduce an acidic gas, for example $CO_2$. Finally, depending on the product desired and its purity, at least one washing step and at least one drying step may also follow.

The second variant for the release of the product under acidic conditions consists in performing a reactive distillation. In this case, the bound ammonium is first released as ammonia and removed, as a result of which the product is finally obtained in pure form.

As a third alternative for the release of the product preferably present as an ammonium salt in the solid, the release within a relatively wide temperature range between 0° C. and 100° C. is proposed. An advisable temperature range in this type of treatment of the product-containing suspension is especially one which is between 20° C. and 80° C., and vacuum conditions may also be suitable. Pressure ranges between 0.1 mbar and 1 bar and in particular between 500 mbar and 800 mbar are considered to be particularly preferred. This essentially thermal elimination can also be performed in the presence of an organic solvent, for example DMF. This latter alternative is the sole exception in which an organic solvent is used in the process claimed.

The driving force for this elimination can be considered to be the solvation pressure, as generally occurs in thermal treatments of organic solutions. In these cases, temperature ranges between 20 and 80° C. and pressures between 1 mbar and 1 bar are advisable. Under these conditions, a clear solution is obtained as a light fraction which is removed, and a second fraction which comprises the desired nitrile dissolved in the solvent.

It is possible with the process according to the invention, consisting of the preparation step 1) and the purification step 2), to obtain in particular benzonitriles with deprotonatable substituents, as represented, for example, by hydroxyl groups, wherein 2-hydroxybenzonitrile and 4-hydroxybenzonitrile, but also 2,4-dihydroxybenzonitrile, are at the forefront. These products feature unique product quality, since they have virtually no impurities resulting from organic solvents and alkylated by-products, the reason for which is especially that they are obtainable by a direct ammonolysis from their acids. The products are thus typically solvent-free amino- and hydroxybenzonitriles. Further advantages of the process according to the invention are considered to be that the most economically viable raw materials are used in each case and that the high yields already addressed are generally achieved as a result of the only very low decarboxylation losses. The ammonia used is utilized efficiently as a result of relatively low discharge rates, associated with low $CO_2$ formation. Since the specific process prevents acidic salt cleavage, no special materials are needed in the industrial scale application of the process proposed, but rather it is generally possible to use inexpensive materials. An additional factor is that chloride-containing wastewaters are avoided, and that the total amount of wastewater can be significantly reduced owing to the specific process.

The examples which follow illustrate the advantages of the process according to the invention.

EXAMPLES

Preparation and purification of 2-hydroxybenzonitrile

1) Preparation Step

For the preparation described below, a supported borophosphate catalyst was used which had been obtained by the following process:

5.88 g of 85% orthophosphoric acid and 3.33 g of 99.8% boric acid were dissolved in 500 g of distilled water. After additional dissolution of 3.6 g of zinc sulfate, this solution was stirred at room temperature for one hour and then 500 g of silica gel whose surface area was>400 m²/g were added;

the pore diameter of the silica gel was between 0.4 nm and 25 nm. Subsequently, the mixture was concentrated by evaporation to dryness under reduced pressure at 60° C. and finally heated to 150° C. while passing a gentle air stream over it for three hours. After cooling, the supported catalyst thus obtained was usable as described below.

50 ml of the zinc-doped supported borophosphate catalyst were introduced into the reactor. Subsequently, 2.1 mol/h of ammonia gas and 350 mmol of 2-hydroxybenzoic acid were introduced into the oxygen-free gas space at a rate of 70 mmol/h at temperatures of 340° C. In a separator, the exiting gas stream was cooled, and the reaction product then separated out as a white flaky solid.

2) Purification Step 500 g of a crude product obtained in preparation step 1) were initially charged and mixed with 1500 ml of aqueous ammonia (as a 32% solution) and then stirred at room temperature for 60 minutes.

The basic suspension obtained from this quench operation was filtered off with suction and the filtercake was washed twice with 187.5 ml of 32% ammoniacal water each time. Subsequently, the filtercake was sucked dry for 20 minutes and admixed with 1250 ml of 15% HCl. Under these acidic conditions, the suspension was stirred at room temperature for 45 minutes, and the solid was filtered off with suction and washed twice with 187.5 ml of 15% HCl each time. The solid was then dried and admixed with 360 ml of demineralized water, stirred for 15 minutes and filtered off with suction. The solid thus obtained was dried at 50° C. overnight using vacuum.

The preparation process and the following purification step afforded 2-hydroxybenzonitrile in yields of 75% of theory with a purity of 98.9%.

The invention claimed is:

1. A process comprising preparing an amino- and hydroxybenzonitrile of the formula (I)

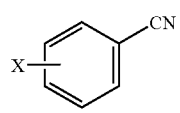
(I)

wherein X is at least one amino or hydroxy group, by reacting an amino- or hydroxybenzoic acid of the general formula (II)

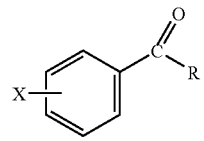
(II)

wherein R is —OH, or NH$_2$, and X is as defined above, with ammonia in the presence of a supported catalyst comprising phosphorus at a temperature between 250 and 500° C., wherein preparation step 1) is performed in a reaction gas that is oxygen free and contains ammonia and without an organic solvent and is then followed by an at least two-stage purification step 2) in which 2.1) the gaseous mixture or solid reaction product obtained from preparation step 1) is converted to an aqueous ammonium-containing suspension and 2.2)

a) releasing the product present in the solid as an ammonium salt with the aid of a filtration by adding acid or by driving out ammonia and subsequently introducing the acid, or b) releasing the product present in the solid as an ammonium salt by reactive distillation, or c) releasing the product present in the solid as an ammonium salt is performed by an elimination at temperatures of from 0 to 100° C. and in the presence of an organic solvent.

2. The process as claimed in claim 1, wherein the process is performed at temperature between 340 and 450° C.

3. The process as claimed in claims 1, wherein the catalyst has been doped with at least one compound comprising a transition metal of group 5, 6, 12 or 14 of the Periodic Table of the Elements and has specific surface area of at least 300 m$^2$/g.

4. The process as claimed in claim 1, wherein the catalyst is doped with boron.

5. The process as claimed in claim 1, wherein the catalyst is a supported boron phosphate catalyst which has been prepared by treating the support material with aqueous solutions of from 0.01 to 15% by weight of phosphoric acid, from 0.01 to 15% by weight of boric acid and from 0.01 to 5% by weight of at lest one salt of transition metal of group 5, 6, 12 or 14 of the Periodic Table of the Elements.

6. The process as claimed in claim 1, wherein the support material comprises at least one compound selected from the group consisting of silicon dioxide, silica gel, aluminum oxide, titanium oxide and zirconium oxide.

7. The process as claimed in claim 1, wherein the salt comprises at least one metal selected from the group consisting of vanadium, niobium, tantalum, chromium, molybdenum, tungsten, cadmium, mercury, germanium, tin, lead or zinc.

8. The process as claimed in claim 7, wherein the salt comprises an anion selected from the group consist of salts consisting of borate, chloride, phosphate and sulfate.

9. The process as claimed in claim 8, wherein the salt comprises ammonium.

10. The process as claimed in claim 1, wherein the specific surface area of the catalyst is>400 m$^2$/g.

11. The process as claimed in claim 1, wherein the catalyst has a pore diameter between 0.4 and 25 nm.

12. The process as claimed in claim 1, wherein the catalyst has been dried at temperatures between 100 and 500° C. for up to 3 hours.

13. The process as claimed in claim 2, wherein the amino- or hydroxybenzoic acid is introduced into the reaction gas (mixture) or the catalyst bed, as a melt, solid or aqueous solution of the ammonium salt.

14. The process as claimed in claim 1, wherein the amino- or hydroxybenzoic acid is introduced into the reaction gas (mixture) or the catalyst bed, as a melt, solid or aqueous solution of the ammonium salt.

15. The process as claimed in claim 1, wherein the purification step 2) is performed at a temperature between −20° C. and 100° C.

16. The process as claimed in claim 1, wherein the purification step 2) is performed under inert gas conditions.

17. The process as claimed in claim 1, wherein the aqueous ammonium-containing suspension is obtained by quenching with the aid of a quench which is performed with water or ammoniacal water.

18. The process as claimed in claim 1, wherein the aqueous ammonium-containing suspension is obtained in the purification step 2) by cooling the product obtained from preparation step 1) and a subsequent absorption with ammoniacal water.

19. The process as claimed in claim 1, wherein the aqueous ammonium-containing suspension is present in highly concentrated form and comprises the by-products in dissolved form.

20. The process as claimed in claim 1, wherein acidic conditions are established in step 2.2) by adding an acid or by introducing an acidic gas.

21. The process as claimed in claim 1, wherein at least one washing step and at least one drying step are effected at the end.

22. The process as claimed in claim 20, wherein the acid is a mineral acid.

23. The process as claimed in claim 22, wherein the mineral acid is hydrochloric acid.

* * * * *